(12) United States Patent
Schmid-Schonbein et al.

(10) Patent No.: US 9,272,034 B2
(45) Date of Patent: Mar. 1, 2016

(54) TREATMENT OF CONDITIONS RELATED TO SHOCK

(75) Inventors: Geert W. Schmid-Schonbein, Del Mar, CA (US); Frank A. DeLano, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 684 days.

(21) Appl. No.: 12/681,510

(22) PCT Filed: Oct. 6, 2008

(86) PCT No.: PCT/US2008/011529
§ 371 (c)(1),
(2), (4) Date: Aug. 9, 2010

(87) PCT Pub. No.: WO2009/045543
PCT Pub. Date: Apr. 9, 2009

(65) Prior Publication Data
US 2010/0303799 A1  Dec. 2, 2010

Related U.S. Application Data

(60) Provisional application No. 60/977,587, filed on Oct. 4, 2007, provisional application No. 60/980,430, filed on Oct. 16, 2007.

(51) Int. Cl.
*A61K 38/48* (2006.01)
*A61K 45/06* (2006.01)
*A61K 31/65* (2006.01)

(52) U.S. Cl.
CPC .............. *A61K 45/06* (2013.01); *A61K 31/65* (2013.01)

(58) Field of Classification Search
None
See application file for complete search history.

(56) References Cited

U.S. PATENT DOCUMENTS

| | | | |
|---|---|---|---|
| 5,171,321 A | 12/1992 | Davis | |
| 5,743,272 A | 4/1998 | Kocher, Jr. | |
| 5,993,427 A * | 11/1999 | Rolland et al. | 604/271 |
| 6,344,189 B1 | 2/2002 | Bunn et al. | |
| 6,455,027 B1 | 9/2002 | Barsky et al. | |
| 6,534,283 B1 | 3/2003 | Schmid-Schoenbein et al. | |
| 6,610,274 B1 | 8/2003 | Gardner | |
| 6,664,287 B2 | 12/2003 | Avery et al. | |
| 8,541,371 B2 | 9/2013 | Schmid-Schonbein et al. | |
| 8,841,258 B2 | 9/2014 | DeLano et al. | |
| 2002/0037265 A1 | 3/2002 | Hung et al. | |
| 2002/0114815 A1 | 8/2002 | Barsky et al. | |
| 2002/0117169 A1 | 8/2002 | Kurz et al. | |
| 2003/0060488 A1 | 3/2003 | Sugiyama et al. | |
| 2004/0014024 A1 | 1/2004 | Yayon et al. | |
| 2005/0037022 A1 * | 2/2005 | Rosen et al. | 424/192.1 |
| 2005/0281772 A1 * | 12/2005 | Bromley et al. | 424/70.14 |
| 2006/0057111 A1 | 3/2006 | Hedlund | |
| 2006/0094727 A1 * | 5/2006 | Gaeta et al. | 514/252.11 |
| 2006/0147439 A1 * | 7/2006 | Upadhyay et al. | 424/94.2 |
| 2006/0153798 A1 * | 7/2006 | Mrsny | 424/85.1 |
| 2006/0211752 A1 * | 9/2006 | Kohn et al. | 514/389 |
| 2006/0216757 A1 * | 9/2006 | Brines et al. | 435/7.2 |
| 2007/0142337 A1 * | 6/2007 | Schmid-Schonbein et al. | 514/152 |
| 2007/0148214 A1 | 6/2007 | Cullen et al. | |
| 2007/0292407 A1 | 12/2007 | Ivanov | |
| 2007/0294107 A1 | 12/2007 | Schmid-Schonbein et al. | |
| 2010/0179091 A1 | 7/2010 | Schmid-Schonbein | |
| 2010/0303799 A1 | 12/2010 | Schmid-Sch nbein | |
| 2011/0039781 A1 | 2/2011 | Schmid-Schonbein | |
| 2013/0158394 A1 | 6/2013 | Hon et al. | |
| 2013/0231309 A1 | 9/2013 | Schmid-Schonbein et al. | |
| 2014/0018293 A1 | 1/2014 | Schmid-Schonbein | |

FOREIGN PATENT DOCUMENTS

| | | |
|---|---|---|
| EP | 1185309 | 3/2002 |
| GB | 2400037 | 10/2004 |
| JP | H7-31829 | 6/1995 |
| JP | 2004-523307 | 8/2004 |
| WO | 2008/103767 | 8/2008 |
| WO | WO 2009/045543 | 4/2009 |
| WO | WO 2009/132149 | 10/2009 |
| WO | 2011/038417 | 3/2011 |
| WO | 2011/088392 | 7/2011 |

OTHER PUBLICATIONS

Bergman et al (Ann. Surg., 205(1): 77-81 (1987).*
Guerciolini (Abstract, 1997).*
The International Bureau of WIPO, International Preliminary Report on Patentability, Apr. 7, 2010, see all.
David Wiseman, Yacov Lyachovetsky, Iian Keidan, J. Richard Trout, Israel Nur, "The Effect of Tranexamic Acid in Firbin Sealant on Adhesion Formation in the Rat," J Biomed Mater Res B Appl Biomater. Feb. 15, 2004, pp. 222-230, 68(2), Synechion, Inc., Dallas, TX, USA.
Deitch E A, Shi H P, Lu Q, et al. "Serine proteases are involved in the pathogenesis of trauma-hemorrhagic shock-induced gut and lung injury." Shock. 2003; 19:452-456.
DeLano and Schmid-Schonbein, "Proteinase activity and receptor cleavage: mechanism for insulin resistance in the spontaneiously hypertensive rat," Hypertension 52:415-23, 2008.
Doucet J J, Hoyt D B, Coimbra R, et al. "Inhibition of enteral enzymes by enteroclysis with nafamostat mesilate reduces neutrophil activation and transfusion requirements after hemorrhagic shock", J Trauma. 2004; 56:501-511.

(Continued)

*Primary Examiner* — Blaine Lankford
*Assistant Examiner* — Thomas J Visone
(74) *Attorney, Agent, or Firm* — Wagenknecht IP Law Group PC

(57) ABSTRACT

Techniques are disclosed for prevention or treatment of physiological shock by administering a specific therapeutic agent, which is able to use smaller volumes of reagent to achieve complete inhibition, than other previously described techniques.

22 Claims, No Drawings

(56) References Cited

OTHER PUBLICATIONS

Fitzal F, DeLano F A, Young C, Rosario H S, Junger W G, Schmid-Schonbein G W. "Pancreatic enzymes sustain systemic inflammation after an initial endotoxin challenge", Surgery, 134:1-11, 2003.

Fitzal F, DeLano F A, Young C, Schmid-Schonbein G W. "Improvement in early symptoms of shock by delayed intestinal protease inhibition", Arch Surg. 2004; 139:1008-1016.

Madan et al., "Use of Ciprofloxacin in the Treatment of Hospitalized Patients with Intra-abdominal Infections", Clinical Therapeutics 26(10):1564-77, 2004.

Muhs B E, Patel S, Yee H, et al. "Inhibition of matrix metalloproteinases reduces local and distant organ injury following experimental acute pancreatitis", J Surg Res. 2003; 109:110-17.

Penn AH, et al., "The Intenstine as Source of Cytotoxic Mediators in Shock: Free Fatty Acids and Degradation of Lipid-Binding Proteins," Am J Physiol Heart Circ Physiol 294:H1779-92, 2008.

Penn, A H, Hugli, T E, Schmid-Schonbein, G W. "Pancreatic enzymes generate cytotoxic mediators in the intestine", Shock 27(3):296-304, 2007.

Rosario H S, Waldo S W, Becker S A, et al. "Pancreatic trypsin increases matrix metalloproteinase-9 accumulation and activation during acute intestinal ischemia-reperfusion in the rat", Am J Pathol. 2004; 164:1707-16.

Saha SK, et al., "Efficacy of Metronidazole Lavage in Treatment of Intraperinoneal Sepsis," Digestive Disease and Science 41(7):1313-18, 1996.

Schmid-Schonbein G W, Hugli T E. "A New Hypothesis for Microvascular Inflammation in Shock and Multiorgan Failure: Self-Digestion by Pancreatic Enzymes", Microcirculation. 2005; 12:71-82.

Schmid-Schonbein G W. 2008 Landis Award lecture—Inflammation and the Autodigestion Hypothesis. Microcirculation, 2009; 16:289-306.

Shi H P, Liu Z J, Wen Y. "Pancreatic enzymes in the gut contributing to lung injury after trauma/hemorrhagic shock", Chin J Traumatol. 2004; 7:36-41. [abstract].

Witek-Janusek and Ratmeyer, "Sepsis in the Young Rat: Maternal Milk Protects During Cecal Ligation and Puncture Sepsis but not During Endotoxemia," Circ Shock 33(4):200-6, 1991.

Aoki, et al. "Blood-brain barrier disruption and matrix metalloproteinase-9 expression during reperfusion injury: mechanical versus embolic focal ischemia in spontaneously hypertensive rats." Stroke 2002, 33:2711-2717.

Arndt et al. "Leukocyte-endothelial cell adhesion in spontaneously hypertensive and normotensive rats." Hypertension 1993, 21: 667-673.

Asanuma et al. "Uniaxial strain upregulates matrix-degrading enzymes produced by human vascular smooth muscle cells." Am J Physiol Heart Circ Physiol 2003, 284: H1778-1784.

Biggs et al. "Tranexamic acid and upper gastrointestinal haemorrhage—a double-blind trial." Gut, 1976, 17: 729-734.

Bursztyn et al. "Insulin resistance in spontaneously hypertensive rats but not in deoxycorticosterone-salt or renal vascular Hypertension." Journal of Hypertension 1992, 10: 137-142.

Cakir et al. "Direct action by doxycycline against canine osteosarcoma cell proliferation and collagenase (MMP-1) activity in vitro." In Vivo 1999,13: 327-331.

Camp et al. "Mechanism of matrix accumulation and glomerulosclerosis in spontaneously hypertensive rats." J Hypertens 2003, 21: 1719-1727.

D'Agostino et al. Doxycycline reduces mortality to lethal endotoxemia by reducing nitric oxide synthesis via an interleukin-10-independent mechanism. J Infect Dis., 1998, 177(2):489-92.

De Lano et al., "A possible role of matrix metalloproteinases in cellular injury of the spontaneously hypertensive rat", FASEB J 2003, 17: A346.330.

De Lano et al. "Control of oxidative stress in microcirculation of spontaneously hypertensive rats." Am J Physiol Heart Circ Physiol 2005, 288: H805-812.

De Lano et al. "Microvascular Display of Xanthine Oxidase and NADPH Oxidase in the Spontaneously Hypertensive Rat." Microcirculation 2006, 13(7):551-66.

De Lano et al. "Enhancement of glucocorticoid and Mineralocorticoid Receptor Density in the Microcirculation of the Spontaneously Hypertensive Rat." Microcirculation 2004, 11: 69-78.

De Lano et al. "Visualization of enhanced matrix metalloproteinase activity in the spontaneously hypertensive rat by a fluorogenic substrate." FASEB J 2005, 19: A1263.

Duivenvoorden et al. "Use of tetracycline as an inhibitor of matrix metalloproteinase activity secreted by human bone-metastasizing cancer cells." Invasion Metastasis 1997, 17: 312-322.

Ergul et al. "Stress upregulates arterial matrix metalloproteinase expression and activity via endothelin: A receptor activation." Am J Physiol Heart Circ Physiol 2003, 285: H2225-2232.

Frears et al. "Inactivation of tissue inhibitor of metalloproteinase-1 by peroxynitrite." FEBS Lett 1996, 381: 21-24.

Galis et al. "Matrix metalloproteinases in vascular remodeling and atherogenesis: the good, the bad, and the ugly." Circ Res 2002, 90: 251-262.

Goldberg et al. "High susceptibility to bacterial infection, butno liver dysfunction, in mice compromised for hepatocyte NF-kappaβ activation." Nature Medicine, 2000, 6(5): 573-577.

Griffin et al. "Reduction of myocardial infarct size by doxycycline: a role for plasmin inhibition." Mol Cell Biochem 2005, 270: 1-11.

Grote et al. "Mechanical stretch enhances mRNA expression and proenzyme release of matrix metalloproteinase-2 (MMP-2) via NAD(P)H oxidase-derived reactive oxygen species." Circ Res 2003, 92: e80-86.

Hanazaki et al. "The protective effect of urinastatin in patients with ileus." Acta Medica et Biologica, 1994, 42(3): 129-132.

Hanemaaijer et al. "Matrix metalloproteinase-8 is expressed in rheumatoid synovial fibroblasts and endothelial cells. Regulation by tumor necrosis factor-alpha and doxycycline."J Biol Chem, 1997, 272: 31504-31509.

Hanemaaijer et al. "Inhibition of MMP Synthesis by Doxycycline and Chemically Modified Tetracyclines (CMTs) in Human Endothelial Cells." Adv Dent Res Nov. 1998, 12:114-118.

Hashimoto et al. "Amyloidosis of the small intestine secondary to rheumatoid arthritis and juvenile rheumatoid arthritis: report of two cases." Rheumatism, Feb. 1995, 35(1): 100-106.

Hulman et al. "Insulin resistance in the conscious spontaneously hypertensive rat: euglycemic hyperinsulinemic clamp study." Metabolism: Clinical and Experimental 1993, 42: 14-18.

Ishimaru et al. "Pancreatic Proteases and Inflammatory Mediators in Peritoneal Fluid During Splanchnic Arterial Occlusion and Reperfusion." Shock 2004, 22(5):467-471.

Kim et al. "Doxycycline inhibits TGF-betal-induced MMP-9 via Smad and MAPK pathways in human corneal epithelial cells." Invest Ophthalmol Vis Sci 2005, 46: 840-848.

Kobayashi et al. "Oxidative stress promotes endothelial cell apoptosis and loss of microvessels in the spontaneously hypertensive rats." Arterioscler Thromb Vasc Biol 2005, 25: 2114-2121.

Kolev et al., "Matrix metalloproteinase-9 expression in post-hypoxic human brain capillary endothelial cells: H.sub.2O.sub.2 as a trigger and NF-kappaB as a signal transducer." Thromb Haemost 2003, 90: 528-537.

Krakauer and Buckley. "Doxycycline is anto-inflammatory and inhibits staphylococcal exotoxin-induced cytokines and chemokines." Antimicrob Agents Chemother, Nov. 2003, 47(11): 3630-3.

Krier et al. "Management of Severe Clostridium difficile-Associated Diarrhea." Digestive Diseases and Sciences, Feb. 19, 2009, 54(6):1199-1202, Kluwer Academic Publishers-Plenum Publishers, NE.

Kuzuya et al. "Role of matrix metalloproteinases in vascular remodeling." J Atheroscler Thromb 2003, 10: 275-282.

Lamparter et al. "Doxycycline and tissue repair in rats." J Lab Clin Med 2002, 139: 295-302.

LE, Jennifer. "Drug Absorption". Merck Manual "Pharmacokinetics in Children" 2010-2013 [retrieved from internet] http://www.merckmanuals.com/professional/print/clinical_pharmacology/pharmacokinetics/drug_absorption_html.

(56) References Cited

OTHER PUBLICATIONS

Lee et al. Doxycycline reduces airway inflammation and hyper-responsiveness in a murine model of toluene diisocyanate-induced asthma. J Allergy Clin Immunol., May 2004, 113(5): 902-9.
Lehoux et al. "Pressure-induced matrix metalloproteinase-9 contributes to early hypertensive remodeling." Circulation 2004, 109: 1041-1047.
Lenda et al. "Reactive oxygen species may contribute to reduced endothelium-dependent dilation in rats fed high salt" Am J Physiol Heart Circ Physiol 2000, 279: H7-H14.
Li et al. "MMP/TIMP expression in spontaneously hypertensive heart failure rats: the effect of ACE- and MMP-inhibition." Cardiovasc Res 2000, 46: 298-306.
Liesenfeld et al. Poster #89, Wound Healing Society, 2006, [retrieved from internet on Mar. 17, 2014] http://content.stockpr.com/qmdt/media/d166915d079a967f12e6c9f114cb0ab.1.pdf.
Lim et al. "Life and death cell labeling in the microcirculation of the spontaneously hypertensive rat." J Vasc Res 2001, 38: 228-236.
Lip et al., "Soluble adhesion molecule P-selectin and endothelial dysfunction in essential Hypertension: implications for atherogenesis? A preliminary report_" Journal of Hypertension 1995,13: 1674-1678.
Masahiro et al. "A case of severe intestinal tuberculosis, treated with ciprofloxacin, kanamycin and prednisolone." Tuberculosis, Apr. 2006, 81(4): 345-349.
Morisco et al. "Insulin-stimulated cardiac glucose uptake is impaired in spontaneously hypertensive rats: role of early steps of insulin signaling." Journal of Hypertension 2000, 18: 465-473.
Mujumdar et al. "Activation of matrix metalloproteinase dilates and decreases cardiac tensile strength." Int J Cardiol 2001, 79: 277-286.
Newaz et al. "Modulation of nitric oxide synthase activity in brain, liver, and blood vessels of spontaneously hypertensive rats by ascorbic acid: protection from free radical injury." Clin Exp Hypertens 2005, 27: 497-508.
Newman et al., "Circular dichroism spectra of tetracycline complexes with Mg+2 and Ca+2." J Pharm Sci 1976, 65: 1728-1732.
Peterson et al. "Matrix metalloproteinase inhibition attenuates left ventricular remodeling and dysfunction in a rat model of progressive heart failure." Circulation 2001, 103: 2303-2309.
Rajagopalan et al. "Reactive oxygen species produced by macrophage-derived foam cells regulate the activity of vascular matrix metalloproteinases in vitro. Implications for atherosclerotic plaque stability." J Clin Invest 1996, 98: 2572-2579.
Rieder et al. "Wound Healing and Fibrosis in Intestinal Disease." Gut, 2007, 56:130-139.
Ritchie. "Protease Inhibitors." Labome Material Methods, 2013, 3(169): 1-7.
Rosenberg et al. "Proteolytic cascade enzymes increase in focal cerebral ischemia in rat" J Cereb Blood Flow Metab 1996, 16: 360-366.
Ryan et al., "Tetracyclines inhibit protein glycation in experimental Diabetes." Adv Dent Res 1998,12: 152-158.
Schmid-Schonbein et al. "Leukocyte counts and activation in spontaneously hypertensive and normotensive rats." Hypertension 1991, 17: 323-330.
Seccia et al. "Extracellular matrix gene expression in the left ventricular tissue of spontaneously hypertensive rats." Blood Press 1999, 8: 57-64.
Sechi et al. "Abnormalities of insulin receptors in spontaneously hypertensive rats." Hypertension 1996, 27: 955-961.
Shen et al. "Circulating leukocyte counts, activation, and degranulation in Dahl hypertensive rats." Circ Res 1995, 76: 276-283.
Shen et al. "Properties of circulating leukocytes in spontaneously hypertensive rats." Biochem Cell Biol 1995, 73: 491-500.
Sironi et al. "Endogenous proteolytic activity in a rat model of spontaneous cerebral stroke." Brain Res 2003, 974: 184-192.
Sorsa et al. "Doxycycline in the protection of serum alpha-1-antitrypsin from human neutrophil collagenase and gelatinase." Antimicrob Agents Chemother 1993, 37: 592-594.

Spiers et al. "Alterations in vascular matrix metalloproteinase due to ageing and chronic Hypertension: effects of endothelin receptor blockade." J Hypertens 2005, 23: 1717-1724.
Spinale, F. G. "Matrix metalloproteinases: regulation and dysregulation in the failing heart." Circ Res 2002, 90: 520-530.
Suematsu et al. "The inflammatory aspect of the microcirculation in Hypertension: oxidative stress, leukocytes/endothelial interaction, apoptosis." Microcirculation 2002, 9: 259-276.
Suematsu et al. "Impairment of selectin-mediated leukocyte adhesion to venular endothelium in spontaneously hypertensive rats." J Clin Invest 1995, 96: 2009-2016.
Sumii et al. "Involvement of matrix metalloproteinase in thrombolysis-associated hemorrhagic transformation after embolic focal ischemia in rats." Stroke 2002, 33: 831-836.
Suzuki et al. "Impaired leukocyte-endothelial cell interaction in spontaneously hypertensive rats." Hypertension 1994, 24: 719-727.
Suzuki et al. "Modification of leukocyte adhesion in spontaneously hypertensive rats by adrenal corticosteroids." J Leukoc Biol 1995, 57: 20-26.
Takase et al. "The inflammatory reaction during venous Hypertension in the rat." Microcirculation 2000, 7: 41-52.
Touyz, R. M. "Reactive oxygen species, vascular oxidative stress, and redox signaling in Hypertension: what is the clinical significance?" Hypertension 2004, 44: 248-252.
Uitto et al. "Doxycycline and chemically modified tetracyclines inhibit gelatinase A (MMP-2) gene expression in human skin keratinocytes." Ann NY Acad Sci 1994, 732: 140-151.
Weiming et al. "Treatment of Early Postoperative Small Intestinal Obstruction." (English Abstract only) Nanjing General Hospital of Nanjing Command, PLA, Clinical School of Nanjing University, 2003, 4:219-222, Nanjing, China.
Wellen and Hotamisligil. "Obesity-induced inflammatory changes in adipose tissue." J Clin Invest., Dec. 2003, 112(12): 1785-8.
Wiseman et al. The Effect of Tranexamic Acid in Firbin Sealant on Adhesion Formation in the Rat. J Biomed Mater Res B Appl Biomater, Feb. 15, 2004, 68(2): 222-230, Synedchion, Inc. Dalls, TX US.
Woods et al. "Oncotic pressure, albumin and ileus: the effect of albumin replacement on postoperative ileus." The American Surgeon, Nov. 1993, 59(11): 758-763.
Yamada et al. "Elastase-like enzyme in the aorta of spontaneously hypertensive rats." Virchows Arch B Cell Pathol Incl Mol Pathol 1983, 44: 241-245.
Yasmin et al. "Matrix metalloproteinase-9 (MMP-9), MMP-2, and serum elastase activity are associated with systolic Hypertension and arterial stiffness." Artenbscler Thromb Vase Biol 2005, 25: 372.
Zweifach et al. "Micropressure-flow relationship in a skeletal muscle of spontaneously hypertensive rats." Hypertension 1981, 3: 601-614.
PCT/US2008/054474 International Search Report and Written Opinion mailed Jun. 27, 2008.
CN201180057633 Office Action mailed Dec. 17, 2013.
CN201180006245 Office Action mailed Apr. 1, 2014.
EP11733481.3 Extended European Search Report mailed Jan. 28, 2015.
EP1830068 Supplementary European Search Report mailed on Mar. 12, 2014.
JP2012-549138 Office Action mailed Sep. 12, 2014.
PCT/US2011/021395 International Search Report mailed Aug. 30, 2011.
Elliott et al. "The Use of Human Serum Albumin in the Management of Acute Pancreatitis: Experimental and Clinical Observations." Gastroenterology, Apr. 1955, pp. 563-592.
Freedman, Steven D. "Acute Pancreatitis: Acute pancreatitis is sudden inflammation of the pancreas that may be mild or life threatening but usually subsides." Merck Manual, Oct. 2012.
O'Brien et al. "Effects of Tranexamic acid and aprotinin, two antifibrinolytic drugs, on PAF-induced plasma extravasation in unanesthetized rats." Inflammation, 2000, 24(5): 411-429.
Yasuda et al. "Treatment strategy against infection: clinical outcome of continuous regional arterial infusion, enteral nutrition, and surgery in severe acute pancreatitis." J Gastroenterol 2007, 42: 681-689.

* cited by examiner

TREATMENT OF CONDITIONS RELATED TO SHOCK

This application is a U.S. national stage application under 35 U.S.C. 371 of the PCT application with Ser. No. PCT/US2008/011529, filed Oct. 6, 2008, which claims priority to U.S. Provisional Patent Application Ser. No. 60/977,587, filed Oct. 4, 2007, and to U.S. Provisional Patent Application Ser. No. 60/980,430, filed Oct. 16, 2007, the contents of all of which are hereby incorporated by reference in their entirety into this disclosure.

GOVERNMENT INTERESTS

This invention was made with government support under HL-10881, HL-067825 and HL-43026 awarded by National Institutes of Health. The government has certain rights in the invention.

BACKGROUND OF THE INVENTION

1. Field of the Invention

The present invention relates to treatment of shock. In particular, the present invention relates to treatment of conditions related to shock.

2. Background of the Invention

Shock is a life-threatening complication in situations associated with trauma including burns, surgery, ischemia, sepsis, and other critical care applications. Shock is a broad term that describes a group of circulatory syndromes, all of which result in general cellular hypoxia. This leads to a depletion of the adenosine triphosphate (ATP), the failure of the sodium-potassium pump, mitochondrial dysfunction, and ultimately the release of a variety of toxic substances, including superoxides. Superoxides are toxic to essentially all tissues. They react with proteins and cause unfolding and are able to induce DNA damage. Additionally, cellular activation in the circulation can be detected by leukocytes or endothelial cells resulting in superoxide production, pseudopod projections, enzyme release, cytokine release, and expression of membrane adhesion molecules. Cell activation fundamentally alters the biomechanics of microvascular blood flow by a shift in rheological, adhesive, and cytotoxic cell properties. Eventually these stress responses give rise to irreversible cardiovascular collapse because of their combined effects on the microcirculation.

There are few satisfactory drugs, treatment methods, or interventions available for the prevention of conditions related to shock. Most currently available methods for the treatment of such conditions related to shock deal with the symptoms, rather than the cause. For this reason, current clinical approaches are limited in their efficacy and can only prevent further damage from occurring.

Thus, there is a need in the art for a more effective treatment of conditions related to shock. The treatment should be simple to administer, effective and capable of aiding in emergency situations.

SUMMARY OF THE INVENTION

The present invention is a technique for treatment of conditions related to physiological shock by administering a more specific combination of therapeutic agents, which is able to use smaller volumes of reagent to achieve complete inhibition, than other previously described methods, for example, that in U.S. Pat. No. 6,534,283, which is incorporated by reference herein in its entirety. The present invention is based upon a new hypothesis for the cause of shock and multi-organ failure: self-digestion through gut ischemic complications rather than bacterial/endotoxin invasion.

The present invention dramatically reduces symptoms of multi-organ failure and mortality in septic shock associated with leakage of cecal material into the peritoneum (e.g., cecal ligation shock). Furthermore, the present invention reduces symptoms of insulin resistance in shock (e.g., septic, hemorrhagic and cecal ligation shock). The methods were tested and verified in various animal studies as discussed below.

In experimental models, it was demonstrated that blockade of pancreatic enzymes in the lumen of the intestine in combination with treatment against cytotoxicity in the peritoneum (blockade of digestive enzymes, binding of cytotoxic mediators and anti-bacterial treatment in the peritoneum) leads to a dramatic enhancement of survival rate in a model of septic shock (cecal ligation model).

In experimental models, it has further been demonstrated that plasma of animals (such as rats) in shock produced by cecal ligation have plasma that exhibits protease activity. The activity is sufficient to cleave the binding domain of insulin on the insulin receptor alpha. Introduction of Futhane and Doxycycline attenuates the insulin receptor cleavage. It is expected that other symptoms of cell and organ dysfunction (such as arterial vasospasm, immune suppression, enhanced permeability, apoptosis, etc.) characteristic for shock will also be attenuated by this treatment.

Such findings lead to the present invention resulting in treatment techniques for prevention of multi-organ failure and mortality in septic shock associated with leaks from intestine during surgery, punctured intestine, ruptured intestinal legions or appendix, or other any other situation associated with leakage of intestinal material (e.g., cecal or fecal matter). Further, such treatments would lead to prevention of the metabolic syndromes in trauma patients and patients in the ICU.

In certain exemplary embodiments, the present invention is a method for prevention or treatment of physiological shock. The method includes administering to a peritoneum of an individual a therapeutic dose of any combination of one or more of: pancreatic digestive enzyme inhibitor, cytotoxic mediator inhibitor, and antibacterial agent.

A method according to the present invention blocks formation of inflammatory mediators by pancreatic digestive enzymes in the intestine in septic shock and thereby reduces symptoms of multi-organ failure and significantly reduces mortality rate. It also serves to reduce morbidity and reduce post-operative complications, enhance recovery rate, and shorten hospital stays.

The treatment is administered into the lumen of the intestine to block fully activated digestive enzymes and auto-digestion of the intestine. The treatment is highly effective to attenuate prolonged formation of inflammation in septic shock, destruction of the intestinal epithelial lining, and reduces mortality. There is currently no comparable treatment for septic shock.

DETAILED DESCRIPTION OF THE INVENTION

This invention describes techniques for treatment of conditions related to shock. Various exemplary embodiments are presented to provide a broad spectrum of treatment available and application to such conditions.

As discussed above, the strategy for inhibiting gut enteral function has been described in U.S. Pat. No. 6,534,283, which is incorporated by reference herein in its entirety. This patent describes the use of protease inhibition in the lumen of the gut in principle and more specifically using specific commercially available protease inhibitors. The current strategy proposes numerous applications related to pancreatic protease inhibitors.

In the present invention, treatment is administered into the lumen of the intestine in combination with a treatment of the peritoneal cavity that can be administered after onset of shock.

In one series of experiments, the inventors discovered that delayed inhibition of digestive enzymes in the lumen of the intestine reduces inflammatory markers after shock. As a clinically relevant situation, the inventors examined the effectiveness of a delayed intestinal protease inhibition during reperfusion after SMAO. Male Wistar rats were exposed to superior mesenteric artery occlusion (SMAO) for 100 min and treated by delayed intestinal lavage beginning 40 min after reperfusion with either buffer or a reversible digestive protease inhibitor (FOY, 0.37 mM). Arterial pressure during reperfusion was significantly lower in shock animals compared with sham shock animals. SMAO and reperfusion without protease blockade caused the formation of leukocyte activation factors in intestinal homogenates and in plasma, as well as intestinal injury and also caused a significant increase in activated leukocytes in venules of cremaster muscle. In contrast, with digestive protease inhibition in the intestine, delayed lavage at 40 min after reperfusion led to a highly significant restoration of the initial blood pressure before shock, decreased formation of intestine-derived leukocyte activation factors and intestinal injury. Delayed digestive enzyme blockade also caused lower leukocytes adhesion in post-capillary venules and reduced cell death in the cremaster muscle microcirculation. Intestinal ischemia-induced endotoxemia was prevented by digestive enzyme inhibition.

In summary, delayed intestinal protease inhibition serves to improve experimental SMAO-induced shock by reducing intestinal injury, the level of cell activation in plasma and in the microcirculation, and by restoring the blood pressure.

Another series of experiments were performed to show that inhibition of pancreatic digestive enzymes in the lumen of the intestine reduces the need for resuscitation in hemorrhagic shock. The inventors examined the utility of intestinal lavage in a porcine model of hemorrhagic shock. An objective of this study was to determine the effect of digestive protease blockade in the lumen of the intestine during hemorrhagic shock. The animals (16 pigs) were subjected to a shock that mimics clinical events. Pigs were bled 30 ml/kg over 30 minutes and maintained at a mean arterial pressure of 30 mmHg for 60 minutes and shed blood was then used to maintain a pressure of 45 mmHg for three hours. Both treated pigs (6-amidino-2-naphthyl p-guanidobenzoate dimethane-sulfate (ANGD), 100 ml/kg of 0.37 mM in GOLYTELY PEG-3350 and electrolytes for oral solution, via a duodenal catheter at 1 liter/hr directly into the lumen of the intestine) and controls (GOLYTELY, PEG-3350 and electrolytes for oral solution, only) had significant reductions in protein and protease levels in the duodenum during enteroclysis, however only ANGD treated animals had persistent suppression of protease activity in the intestinal lumen and in plasma throughout the experiment. Pigs with blockade of digestive enzymes had a major reduction of transfusion requirement of shed blood (18.1±4.5 ml/kg versus 30±0.43 ml/kg; p=0.002), a significantly lower level of neutrophil activation than controls after resuscitation (31.1±3.3% versus 46.9±4.5% in controls, p=0.0002). Leukocyte infiltration into the lung was lower in treated than control animals (p=0.04) and the liver and small intestine showed less injury in treated animals. In summary, a digestive enzyme inhibitor given via enteroclysis significantly reduces leukocyte activation and transfusion requirements during resuscitation from hemorrhagic shock.

In another series of studies, the inventors show that blockage of digestive enzymes in the lumen of the intestine attenuates microvascular inflammation in peripheral organs. These experiments were designed to examine whether inflammatory mediators generated in the intestine by digestive enzymes are released early into the circulation and may contribute to the severe systemic inflammatory response syndrome during shock, a condition that involves the microcirculation in peripheral organs. Intestinal ischemia and reperfusion-induced hypotension upon reperfusion was accompanied by a significant increase in the level of neutrophil activating factors in the intestine and plasma. During reperfusion a significant increase in leukocyte-endothelium interactions in post-capillary venules and parenchymal cell death are observed in the cremaster muscle in controls after SMAO. In contrast, intra-intestinal pancreatic protease inhibition (gabexate mesilate, 0.37 mM) results in a stable blood pressure throughout the experiment. Cell activation and leukocyte-endothelial interactions, both in term of rolling and firm adhesion to the endothelium and cell death (as measured by propidium iodine labeling) in the cremaster muscle, were almost completely abolished after blockade with gabexate mesilate. In addition, ischemia-induced intestinal mucosal injury is attenuated with intestinal pancreatic protease inhibition. In conclusion, intestinal pancreatic protease inhibition significantly attenuates intestinal ischemia-induced shock by reducing the systemic inflammatory response syndrome.

In another series of experiments, the inventors show that digestive enzyme blockade is protective against inflammation in shock if placed inside the lumen of the intestine and less by intravenous administration. From a mechanistic point of view, an important feature is the fact that the significant protection rendered by the inhibition of pancreatic digestive enzymes is only provided if the enzymes are blocked inside the lumen of the intestine. If the enzyme inhibitors are administered directly into the circulation (i.v., i.a., i.m.), less, and in some cases no protection is achieved, a feature that has been confirmed using different protease inhibitors (ANGD and aprotinin). This observation supports the hypothesis that digestive enzymes in the lumen of the intestine—where they are fully activated and in high concentrations—are the major enzymes in acute intestinal ischemia. They produce inflammatory mediators that are carried towards the central circulation via the portal venous system, but also via the intestinal lymphatics. Besides the portal venous circulation and the intestinal lymphatics, the inventors showed that inflammatory mediators can also be carried directly across the intestinal wall into the peritoneal cavity, along a third major pathway.

In another study, the inventors show that digestive enzymes mediate microvascular inflammation in septic shock. Sepsis is accompanied by severe inflammation whose mechanism remains uncertain. The inventors examined the possibility that pancreatic digestive enzymes may also be involved in inflammation in an experimental form of septic shock with a lethal dose of endotoxin in the rat. Immediately after intravenous endotoxin administration, the small intestine was subjected to intra-luminal lavage with and without an inhibitor of pancreatic digestive proteases (FOY, gabexate mesilate). After endotoxin administration (4 mg/kg, gram-negative), control rats developed hypotension, tachycardia, hyperventilation and leukopenia. The intestine and plasma contained mediators that activated leukocytes. The leukocyte-endothelial interaction within the cremaster muscle microcirculation was enhanced. Endotoxin administration resulted in elevated IL-6 plasma levels and histological evidence indicates liver and intestinal injury. In contrast, blockade of pancreatic proteases in the intestinal lumen significantly improved hemodynamic parameters and reduces all indices of inflammation in plasma as well as cell injury in peripheral skeletal muscle microcirculation. These experiments indicate that inflammatory mediators derived from the intestine by digestive proteases may be involved in the prolonged inflammatory response and may sustain symptoms of sepsis after an endotoxin challenge. A bolus administration of endotoxin causes a transient inflammation response and elevated intestinal permeability. But the sustained inflammation that leads to multi-organ failure in this situation is caused by auto-digestion due to escape of pancreatic digestive enzymes from the lumen of the intestine due to the elevated mucosal permeability.

A study of the long term survival after blockade of digestive enzymes provided further support to the findings. In preparation for this application the inventors carried out pilot studies in the rat with (a) hemorrhagic, (b) endotoxic and (c) cecal ligation shock, followed by an observation period for two weeks until normal cage activities were recorded in survivors. Without food restriction, in hemorrhagic shock the mean blood pressure was reduced for two hours to 35 mmHg followed by return of all blood volume but no further resuscitation. The digestive enzymes were blocked at 1 hour after hypotension by direct infusion of ANGD (0.37 mM, 15 ml) into the intestinal lumen after a temporary exposure via a midline incision. In endotoxic shock, the rats received gram-negative endotoxin (5 mg/kg, i.v.); the digestive enzymes were blocked in the same way at 1 hour after endotoxin administration. No other agent was administered. In cecal ligation shock both the digestive enzymes in the lumen of the intestine as well as inside the peritoneum were blocked with ANGD. Untreated controls in each model of shock had high mortality (within less than 8 hours), while blockade of the digestive enzymes ANGD in each shock model lead to a significantly enhanced survival rate (Table I). In contrast to untreated controls, all treated survivors returned after anesthesia within hours to normal activity (walking, climbing, grooming, drinking, eating, bowel movements) and within 3 days to normal weight gain. Furthermore, treatment with alternative serine protease inhibitors (CYCLOKAPRON, tranexamic acid; TRASYLOL, aprotinin) in cecal ligation shock gave significant survival rates (5/5 rats, $P<0.0079$; 4/5 rats, $P<0.02$, respectively).

the extracellular domain of the insulin receptor a by using an antibody against the extracellular binding domain of insulin combined with membrane receptor density measurements. Exposure of normal donor cells to plasma from shock rats, but not to plasma of control rats, causes extensive cleavage of the insulin binding domain. Furthermore, this cleavage causes also a reduction of the glucose transport into the cell cytoplasm. These results show that the plasma enzymatic activity may be responsible for the development of insulin resistance typical for patients in shock. The activity can be significantly blocked with ANGD (by more than 50%, results not shown), suggesting that proteases are a major component of this enzyme activity. There is also a significant cleavage of the extracellular domain of the tight junction protein E-cadherin in intestinal epithelium and CAT-1 in leukocytes.

Another recent study by the inventors, listed as item (9) below, and which is incorporated by reference herein in its entirety, showed that pancreatic enzymes generate cytotoxic mediators in the intestine. And, thus, there exists a link between the permeability increase in the intestinal wall and the early stages of shock with formation of inflammatory and cytotoxic factors. These factors may either be already present in form of digested food or may be created by action of digestive enzymes on interstitial structures after entry into the intestinal wall and may cause the intestinal necrosis observed in shock. We have shown that both individual serine proteases and fluid from the lumen of the intestine with endogenous proteases have the ability to generate cytotoxicity from intestinal wall homogenates and that luminal fluid may also generate cytotoxicity from homogenized food. These findings further support the hypothesis that lavage of the content of the small intestine with broad-spectrum inhibitors may be protective in shock, in line with experimental evidence. There is a need to identify the actual biochemical structure of the cytotoxic factors and determine their mechanism of action.

In another follow up study, listed as item (10) below and incorporated by reference herein in its entirety, the inventors sought to show that the intestine is a source of cytotoxic mediators in shock, and the role of free fatty acids and degradation of lipid-binding proteins. In this study, the inventors showed that using chloroform/methanol separation of rat small intestine homogenates into lipid fractions and aqueous and sedimented protein fractions and measuring cell death caused by those fractions, it was found that the cytotoxic factors are lipid in nature. Recombining the lipid fraction with

TABLE I

Long-Term Survival Following Shock With and Without Intra-Intestinal Enzyme Blockade*

| (A) Hemorrhagic Shock[1] | | | (B) Endotoxic Shock[2] | | | (C) Cecal Lig. Shock[3] | | |
|---|---|---|---|---|---|---|---|---|
| | Non-Survivor | Survivor | | Non-Survivor | Survivor | | Non-Survivor | Survivor |
| Untreated | 9 | 3 | Untreated | 9 | 4 | Untreated | 9 | 1 |
| ANGD Treated | 2 | 10 | ANGD Treated | 1 | 10 | ANGD Treated | 1 | 9 |

*number of rats
[1] $P < 0.01$
[2] $P < 0.004$
[3] $P < 0.001$ by Fisher's Exact Test It was further shown that plasma of shock rats has protease activity and causes cleavage of the extracellular domain of the insulin receptor, E-cadherin, and CAT-1. In all forms of shock there is consistently proteolytic activity in plasma. Therefore the inventors investigated the ability of central venous plasma of rats in hemorrhagic shock (collected at 4 hours) to cleave protein fractions prevented cell death, except when homogenates were protease digested. Using a fluorescent substrate, the inventors found high levels of lipase activity in intestinal homogenates and cytotoxic levels of free fatty acids. Addition of albumin, a lipid binding protein, prevented cell death, unless the albumin was previously digested with protease.

Homogenization of intestinal wall in the presence of the lipase inhibitor orlistat prevented cell death after protease digestion. In vivo, orlistat plus the protease inhibitor aprotinin, administered to the intestinal lumen, significantly improved survival time compared with saline in a splanchnic arterial occlusion model of shock. These results indicate that major cytotoxic mediators derived from an intestine under in vitro conditions are free fatty acids (FFAs). Breakdown of free fatty acid binding proteins by proteases causes release of free fatty acids to act as powerful cytotoxic mediators.

The discovery further includes clarification of the mechanism that leads to insulin resistance. It is shown that one of the ways that the present invention works is due to enzymatic cleavage of the insulin binding-domain, and introduction of proteases attenuates the process.

There is currently no generally accepted treatment algorithm or protocol for treatment of insulin resistance in shock. Limited options include insulin administration.

In another recent study, listed as item (11) below and incorporated by reference herein in its entirety, the inventors showed that there is a relationship between proteinase activity and receptor cleavage and that there appears to be a mechanism for insulin resistance in the spontaneously hypertensive rat. The inventors hypothesized that enhanced proteolytic activity in the microcirculation of spontaneously hypertensive rats (SHRs) may be a pathophysiological mechanism causing cell membrane receptor cleavage and examined this for 2 different receptors. Immunohistochemistry of matrix-degrading metalloproteinases (matrix metalloproteinase [MMP]-9) protein showed enhanced levels in SHR microvessels, mast cells, and leukocytes compared with normotensive Wistar-Kyoto rats. In vivo microzymography shows cleavage by MMP-1 and -9 in SHRs that colocalizes with MMP-9 and is blocked by metal chelation. SHR plasma also has enhanced protease activity. The inventors demonstrated with an antibody against the extracellular domain that the insulin receptor-$\alpha$ density is reduced in SHRs, in line with elevated blood glucose levels and glycohemoglobin. There is also cleavage of the binding domain of the leukocyte integrin receptor CD18 in line with previously reported reduced leukocyte adhesion. Blockade of MMPs with a broad-acting inhibitor (doxycycline, 5.4 mg/kg per day) reduces protease activity in plasma and microvessels; blocks the proteolytic cleavage of the insulin receptor, the reduced glucose transport; normalizes blood glucose levels and glycohemoglobin levels; and reduces blood pressure and enhanced microvascular oxidative stress of SHRs. The results suggest that elevated MMP activity leads to proteolytic cleavage of membrane receptors in the SHR, e.g., cleavage of the insulin receptor-binding domain associated with insulin resistance.

Further, there is currently no generally accepted treatment algorithm or protocol for septic shock. There is an FDA approved treatment with activated protein C (XIGRIS, drotrecogin alfa (activated), Eli Lilly), which gives a minor but confirmed survival benefit. However, even such treatment has been called into question as more recent trials could not confirm the effectiveness of activated protein C.

Treatment of septic shock is based on supportive care by treating the underlying infection (appropriate antibiotics within the first 4-8 hours of presentation) and on restoring tissue perfusion with a combination of fluid resuscitation (e.g., albumin, lactated or hypertonic saline) and vasopressor administration (e.g., noreinephrine).

In an exemplary embodiment, the present invention involves several components, which may be performed independently or in combination. One component of a treatment according to the present invention includes administration of a pancreatic enzyme inhibitor directly into the lumen of the intestine (by oral administration, introduction via an esophageal catheter, direct injection into the lumen of the intestine during surgery, etc). The agents to be used individually or in combination include but are not limited to: FUTHAN, nafamostat mesilate (0.37 mM); TRASYLOL, aprotinin (Bayer) (1.4 mg/ml), serine protease inhibitor; CYKLOKAPRON, tranexamic acid (Pfizer) (1.4 mg/ml), serine protease inhibitor; broad based MMP inhibitors (e.g., doxycycline); orlistat (5 to 50 mg/ml), lipase inhibitor; plus any other pancreatic enzyme inhibitor. The amount administered may be adjusted according to intestine size and enzyme levels to achieve complete blockade of digestive enzyme activity.

A second component of a treatment according to the present invention includes treatment of the peritoneum by a combination of three protective interventions: blockade of pancreatic digestive enzymes (serine proteases, lipases, as outlined in the first component described above); blockade of cytotoxic lipid derived mediators (e.g., free fatty acids) with free fatty acid binding proteins (e.g., albumin, and others); antibacterial treatment against gram-positive and gram-negative bacteria that have entered into the peritoneal space (with antibiotic treatment, e.g., ciprofloxacin, metronidazole, imipenem and cilastatin, ticarcillin and clavulanate, cefuroxime). Further effectiveness of the treatment is achieved by peritoneal/intraintestinal lavage in combination with the treatments listed above.

The administration of the serine proteases and MMPs with broad spectrum blockers, as outlined in the first component described above, may be alternatively or additionally performed through an intravenous (i.v.) route.

The present invention may be used in numerous medical treatments, including but not limited to, treatment for prevention of multi-organ failure and mortality in septic shock. Any lipase inhibitor in combination with a pancreatic or leukocyte derived protease inhibitor may have utility to prevent inflammation in septic shock.

In one exemplary embodiment, which may be used for treatment for prevention of post-operational complications, including multi-organ failure, sepsis, morbidity, and mortality, pancreatic protease inhibition is initiated to reduce complications and hospital stay after trauma/surgery. Here, it has been shown that pancreatic enzymes in the intestine have the ability to generate powerful inflammatory mediators and that blockade of pancreatic enzymes in the lumen of the intestine attenuates inflammatory symptoms after different shock models.

In this embodiment, the present invention allows a reduction in inflammatory symptoms and complications (swelling, embolism formation, selected organ dysfunction, pulmonary embolism, incidence of stroke, patient mobility, morbidity, multi-organ failure, mortality) in any form of elective surgery/general anesthesia associated with elevated risks (such as prolonged surgery procedures, surgery with bypass requirements, surgery on patients with preconditions and risk factors, surgery involving the intestine and pancreas). This results in a reduction in post-surgical complications, enhance wound healing, reduce total recovery period, and reduce hospitalization requirements and time.

In elective surgery, pre-administration of a pancreatic enzyme inhibitor may be conducted directly into the lumen of the intestine (by oral administration, introduction via an esophageal catheter, direct injection into the lumen of the intestine during surgery). The agents to be used are individually or in combination: FUTHAN, nafamostat mesilate (0.1 mM); TRASYLOL, aprotinin (Bayer) (1.4 mg/ml), serine protease inhibitor; CYKLOKAPRON, tranexamic acid (1.4 mg/ml), serine protease inhibit orlistat (5 to 50 mg/ml), lipase inhibitor plus any other pancreatic enzyme inhibitor. The amount administered is adjusted according to intestine size to achieve complete blockade of digestive enzyme activity. The inhibitor is administered prior to general anesthesia/surgery as pretreatment.

This is the first intervention against a major source of inflammation in multi-organ failure associated with surgery/general anesthesia. Blockade of digestive enzymes prior to general anesthesia may serve to preserve barrier properties of the intestinal mucosa, reduce inflammation in the central circulation, and consequently reduce recovery and wound healing periods, post-surgical complications, hospital stays, etc.

A potentially useful application of the digestive enzyme inhibition as pre-treatment is for patients subjected to radiation or chemotherapeutic treatment. It could also work for radiation treatment under other circumstances to reduce symptoms of multi-organ failure.

In another exemplary embodiment, the present invention provides a method for pancreatic protease inhibition in septic shock. There are many uses for this embodiment, including but not limited to, treatment for prevention of multi-organ failure and mortality in septic shock. Such treatment works by blocking formation of inflammatory mediators by pancreatic digestive enzymes in the intestine in septic shock and thereby reducing symptoms of multi-organ failure and mortality.

The treatment is administered into the lumen of the intestine to block fully activated digestive enzymes and auto-digestion of the intestine. The treatment is highly effective to attenuate prolonged formation of inflammation in septic shock, destruction of the intestinal epithelial lining, and reduces mortality.

It is demonstrated that blockade of pancreatic enzymes in the lumen of the intestine attenuates inflammatory symptoms after administration of a lethal dose of endotoxin (6 mg/kg). Experiments demonstrate reduced long-term mortality in the same sepsis model.

Administration of a pancreatic enzyme inhibitor may be conducted directly into the lumen of the intestine (by oral administration, introduction via an esophageal catheter, direct injection into the lumen of the intestine during surgery). The agents to be used are individually or in combination: FUTHAN, nafamostat mesilate (0.1 mM); TRASYLOL, aprotinin (1.4 mg/m), serine protease inhibitor; orlistat (5 to 50 mg/ml), lipase inhibitor; plus any other pancreatic enzyme inhibitor. The amount administered is adjusted according to intestine size to achieve complete blockade of digestive enzyme activity.

In another exemplary embodiment, the present invention is used for pancreatic lipase inhibition to reduce mortality after shock. This embodiment is very useful for developing treatment for prevention of multi-organ failure and mortality in hemorrhagic shock, preventive treatment to reduce the probability for development of multi-organ failure in elective surgery, long-term treatment to reduce production of lipid derived inflammatory mediators associated in chronic diseases. It is also particularly useful because there does not appear to be any treatment proposed to attenuate inflammation by blockade of lipase activity in the intestine in either acute or chronic inflammatory conditions.

This embodiment is designed as an intervention to block the lipase activity in the lumen of the intestine and also in the general circulation in those cases in which lipase enters from the lumen of the intestine into the circulation. This prevents formation of lipid derived inflammatory or cytotoxic mediators in shock and other inflammatory diseases and attenuate multi-organ failure in shock and chronic inflammation in diseases like hypertension, diabetes, the metabolic syndrome, cancers and in chronic degenerative diseases.

Recent evidence resulting in this invention suggests that a major component of inflammatory mediators from the intestine in shock causing multi-organ failure and mortality (e.g., after surgery/general anesthesia, trauma, chronic diseases and any other condition leading multi-organ failure) is derived from the action of pancreatic lipases (lipid splitting enzymes). Blockade of pancreatic lipase serves to reduce mortality during shock and reduce inflammation that leads to multi-organ failure. Blockade of pancreatic lipase prior to general anesthesia may serve to preserve barrier properties of the intestinal mucosa, reduce inflammation in the central circulation, and consequently reduce recovery and wound healing periods, post-surgical complications, hospital stays, etc.

The inventors have shown that the ischemic intestine produces a powerful set of lipid derived cytotoxic mediators and that the blockade of lipase in the intestine under in-vitro conditions blocks the production of lipid-derived cytotoxic mediators.

In elective surgery, pre-administration of a pancreatic enzyme inhibitor directly into the lumen of the intestine (by oral administration, introduction via an esophageal catheter, direct injection into the lumen of the intestine during surgery) may have a positive effect on recovery. The agents to be used are individually or in combination: orlistat (5 to 50 mg/ml), lipase inhibitor; plus any other pancreatic enzyme inhibitor. The amount administered is adjusted according to intestine size and content to achieve complete blockade of digestive enzyme activity. As treatment the inhibitor is administered after trauma or sepsis associated with risk for shock and multi-organ failure. As pretreatment the inhibitor is administered prior to general anesthesia/surgery.

The above exemplary embodiments have shown various uses and techniques for decreasing certain conditions related to shock. Thus, as a whole, the present invention is based on data from animal studies that show dramatic reduction in life-threatening shock by inhibiting a body's own aggressive digestive enzymes. This novel approach targets trigger mechanisms in auto-digestion before it launches lethal inflammatory cascade.

Death from heart, lung and kidney failure during shock due to inadequate blood flow can be prevented by an unusual experimental treatment that inhibits the aggressive enzymes that are produced in body to digest food.

The invention provides evidence from recent animal studies that for the first time, studies showed that blockade of the digestive enzymes during shock leads to long-term survival. The results show a dramatic reduction of mortality in hemorrhagic shock induced multi-organ failure. This treatment holds great promise for future clinical application, particularly in emergency rooms and before high-risk surgeries. When a person is in shock, his or her life is on the line. The patient's survival may be in jeopardy not just that day, but within an hour because healthy organs can fail and die in rapid succession.

An estimated 1 million cases of various types of shock are treated annually in U.S. hospital emergency rooms. Shock is a serious medical condition with a fatality rate of approximately 29%. While the optimal management of shock patients can improve survival rates, overall shock remains a condition with a high death rate.

Administering a drug to inhibit the body's digestive enzymes is a relatively new approach that was begun in the past decade. In 1998 a finding was made in laboratory studies on the body's inflammatory cascade and the factors that turn this normal tissue-healing biological process into a virulent, out of control firestorm against the body's normal tissue.

The researchers then began animal studies. The present invention is based on the latest research using rodent models of human hemorrhagic shock. Here it has been discovered that the sudden lowering of blood pressure that occurs in people suffering from stroke can provoke the body's digestive enzymes to break down the body's own intestinal tissue as if it were food. Such enzymes' abnormal actions may be defined as "auto-digestion." Auto-digestion is dangerous because not only does it injure healthy tissue but also contributes to multi-organ failure, which can be fatal.

The healthy cells of the animals' intestinal tissue react to auto-digestion by releasing a slew of substances that can be toxic to the heart and other body organs. These substances, termed cytotoxic mediators, can reach these body organs via the blood stream. In their latest studies, shock was induced in 19 lab rodents, all of which were then treated with therapies that mirror the emergency room care given to many human patients who suffer shock, which typically occurs when blood flow to the heart, lungs and other body organs is slowed as a result of trauma, dehydration, heart attack or stroke.

A total of 10 of the 19 lab rodents in shock were also treated with the experimental digestive enzyme inhibitor called ANGD. Eight of the ten survived. However, only one of the nine "untreated" animals in shock survived. The other eight animals died from organ failure within 12 hours. Although these "untreated" animals did not receive ANGD, the inhibitor, they were given basic shock care. The enzyme inhibitor ANGD dramatically improved the survival rate among the lab animals in which shock had been induced.

In the pig studies, the scientists also are conducting experiments to identify the time period when the experimental treatment will be the most effective in saving lives. The findings will be relevant to the emergency care of human patients in shock. Data indicate that the early the treatment occurs, the better the chances for survival. Current research indicates that the window of opportunity for the treatment to be effective does not seem to be very narrow.

The discovery of the "auto-digestion" process and their positive findings from the experimental treatment ANGD are based on National Institutes of Health funded basic research to determine the origin of the inflammatory cascade that causes organ failure and death. Basically, inflammatory is the body's mechanism to repair, to heal tissue. But in shock, the inflammation never stops. It is out of control. Normally the body senses when the inflammatory process has completed its job and brings it to a halt.

There is little surprise that tissue can be severely damaged by the actions the body's digestive enzymes, which are secreted by the pancreas but do not become activated until they arrive into the intestines. Digestive enzymes have to be very aggressive, and there has to be lots of them, for the body to efficiently digest, to break down, the food that we eat. Normally the intestinal tissue is protected from these enzymes by a layer of secreted mucus and by the tight packing of the cells in the intestinal wall. The enzymes are too big to defuse between these cells under normal conditions.

The following references, some as cited above, are hereby incorporated by reference herein in their entirety into this disclosure:

1. Schmid-Schonbein G W, Hugli T E. A New Hypothesis for Microvascular Inflammation in Shock and Multiorgan Failure: Self-Digestion by Pancreatic Enzymes. *Microcirculation*. 2005; 12:71-82.
2. Doucet J J, Hoyt D B, Coimbra R, et al. Inhibition of enteral enzymes by enteroclysis with nafamostat mesilate reduces neutrophil activation and transfusion requirements after hemorrhagic shock. *J Trauma*. 2004; 56:501-511.
3. Fitzal F, DeLano F A, Young C, Schmid-Schonbein G W. Improvement in early symptoms of shock by delayed intestinal protease inhibition. *Arch Surg*. 2004;139: 1008-1016.
4. Deitch E A, Shi H P, Lu Q, et al. Serine proteases are involved in the pathogenesis of trauma-hemorrhagic shock-induced gut and lung injury. *Shock*. 2003;19:452-456.
5. Shi H P, Liu Z J, Wen Y. Pancreatic enzymes in the gut contributing to lung injury after trauma/hemorrhagic shock. *Chin J Traumatol*. 2004; 7:36-41.
6. Muhs B E, Patel S, Yee H, et al. Inhibition of matrix metalloproteinases reduces local and distant organ injury following experimental acute pancreatitis. *J Surg Res*. 2003;109 :110-7.
7. Rosario H S, Waldo S W, Becker S A, et al. Pancreatic trypsin increases matrix metalloproteinase-9 accumulation and activation during acute intestinal ischemia-reperfusion in the rat. *Am J Pathol*. 2004;164:1707-16.
8. Fitzal F, DeLano F A, Young C, Rosario H S, Junger W G, Schmid-Schönbein G W. Pancreatic enzymes sustain systemic inflammation after an initial endotoxin challenge. *Surgery*, 134:446-456, 2003.
9. Penn, A H, Hugli, T E, Schmid-Schönbein, G W. Pancreatic enzymes generate cytotoxic mediators in the intestine. *Shock*, Vol. 27, No. 3, pp. 296-304, 2007.
10. Penn, A H, Schmid-Schönbein, G W. The intestine as source of cytotoxic mediators in shock: free fatty acids and degradation of lipid binding proteins. *Am J Physiol Heart Circ Physiol* 294: H1779-H1792, 2008.
11. DeLano, F A, Schmid-Schönbein, G W. Proteinase activity and receptor cleavage: mechanism for insulin resistance in the spontaneously hypertensive rat. *Hypertension*. 2008;52:415-423.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method for prevention or treatment of physiological shock in an individual comprising administering to the lumen of an intestine of the individual a therapeutic dose of a combination of a pancreatic digestive enzyme inhibitor, a cytotoxic mediator inhibitor, an MMP inhibitor, and an antibacterial agent.

2. The method of claim 1, wherein the MMP inhibitor comprises doxycycline.

3. The method of claim 1, further comprising:
administering to the lumen of the intestine of the individual a therapeutic dose of one or more of a serine protease inhibitor and a lipase inhibitor.

4. The method of claim 1, wherein the pancreatic digestive enzyme inhibitor comprises a serine protease inhibitor.

5. The method of claim 1, wherein the pancreatic digestive enzyme inhibitor comprises a lipase inhibitor.

6. The method of claim 1, wherein the cytotoxic mediator is lipid derived.

7. The method of claim 6, wherein the cytotoxic lipid derived mediator inhibitor comprises free fatty acid binding proteins.

8. The method of claim 7, wherein the free fatty acid binding protein comprises albumin.

9. The method of claim 1, wherein the antibacterial agent comprises an antibiotic agent.

10. The method of claim 9, wherein the antibiotic agent comprises one or more of ciprofloxacin, metronidazole, imipenem, cilastatin, ticarcillin, clavulanate, or cefuroxime.

11. A method for prevention or treatment of physiological shock in an individual comprising administering to the lumen of an intestine of the individual a therapeutic dose of a combination of a pancreatic digestive enzyme inhibitor and a cytotoxic mediator inhibitor, and administering to the lumen of the intestine of the individual a therapeutic dose of an MMP inhibitor.

12. The method of claim 1, wherein the administering to the lumen of the intestine is by oral administration.

13. The method of claim 1, wherein the administering to the lumen of the intestine is by esophageal catheter.

14. The method of claim 1, wherein the administering to the lumen of the intestine is by duodenal catheter.

15. The method of claim 1, wherein the administering to the lumen of the intestine is by direct injection into the intestine.

16. The method of claim 1, wherein the pancreatic digestive enzyme inhibitor is selected from the group consisting of 6-amidino-2-napthyl p-guanidobenzoate dimethane-sulfate (ANGD), gabexate mesilate, tranexamic acid, aprotinin, and orlistat.

17. The method of claim 5, wherein the lipase inhibitor is orlistat.

18. The method of claim 11, wherein the administering to the lumen of the intestine is by oral administration.

19. The method of claim 11, wherein the administering to the lumen of the intestine is by esophageal catheter.

20. The method of claim 11, wherein the administering to the lumen of the intestine is by duodenal catheter.

21. The method of claim 11, wherein the administering to the lumen of the intestine is by direct injection into the intestine.

22. The method of claim 11, wherein the pancreatic digestive enzyme inhibitor is selected from the group consisting of 6-amidino-2-napthyl p-guanidobenzoate dimethane-sulfate, nafamostat mesilate, gabexate mesilate, tranexamic acid, aprotinin, and orlistat.

* * * * *